//  US Patent 5,080,905

United States Patent [19]
Pestellini et al.

[11] Patent Number: 5,080,905
[45] Date of Patent: Jan. 14, 1992

[54] THERAPY OF 10-AMINO-5,6-DIHYDRO-11H-DIBENZO(B,E)AZEPINE-6,11-DIONE AND DERIVATIVES AS DRUGS FOR USE IN THE TREATMENT OF URINARY INCONTINENCE

[75] Inventors: Vittorio Pestellini; Carlo A. Maggi; Alberto Meli; Giovanni Viti, all of Florence, Italy

[73] Assignee: A. Menarini Industrie Farmaceutiche Riunite s.r.l., Florence, Italy

[21] Appl. No.: 552,786

[22] Filed: Jul. 12, 1990

[30] Foreign Application Priority Data

Jul. 14, 1989 [IT] Italy .................. 9484 A/89

[51] Int. Cl.⁵ .............................. A61K 9/48
[52] U.S. Cl. ...................... 424/451; 514/213; 128/DIG. 25; 128/748
[58] Field of Search .......... 128/DIG. 25, 748; 514/213

[56] References Cited

U.S. PATENT DOCUMENTS

| | | | |
|---|---|---|---|
| 3,646,616 | 3/1972 | Keshin | 128/DIG. 25 |
| 4,011,319 | 3/1977 | Kaiser | 514/213 |
| 4,790,328 | 12/1988 | Young | 128/748 |

FOREIGN PATENT DOCUMENTS 0089322  3/1983  European Pat. Off. .

*Primary Examiner*—Thurman K. Page
*Assistant Examiner*—William E. Benston
*Attorney, Agent, or Firm*—McGlew & Tuttle

[57] ABSTRACT

Use of a 10-amino-5,6-dihydro-11H-dibenzo(b,e)azepine-6,11-dione of formula I

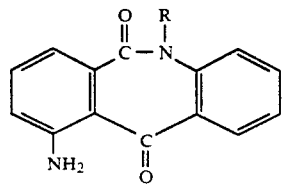

where R represents an atom of hydrogen or a lower alkyl group, especially containing from 1 to 5 carbon atoms, as well as of a therapeutically acceptable salt of said compound, to prepare a drug for use in the treatment of urinary incontinence.

22 Claims, No Drawings

THERAPY OF 10-AMINO-5,6-DIHYDRO-11H-DIBENZO(B,E)AZEPINE-6,11-DIONE AND DERIVATIVES AS DRUGS FOR USE IN THE TREATMENT OF URINARY INCONTINENCE

DESCRIPTION

The present invention relates to the therapeutic use, in the treatment of urinary incontinence, of a 10-amino-5,6-dihydro-11H-dibenzo(b,e)azepine-6,11-dione of general formula I

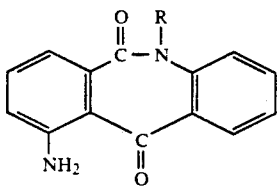

where R represents an atom of hydrogen or a lower alkyl group, as well as of a therapeutically acceptable salt of said compound. The term lower alkyl group is used to mean an alkyl radical containing from 1 to 5 atoms of carbon and, preferably, methyl. By therapeutically acceptable salt of a compound of formula I is meant a salt obtained by the addition of an acid, such as, for example, hydrochloric or sulfuric acid.

The 10-amino compound of formula I, in which R=H, is already known and described in the literature as an intermediate in chemical syntheses (Gazz. Chim. It. 83, 533, 1953).

The N-alkylated derivatives, in which R=lower alkyl, are either already known or can easily be prepared by simple alkylation using well-known methods described in the literature.

From European Patent No. 0089322 it is known that 10-amino-5,6-dihydro-11H-dibenzo(b,e)azepin-6-ones are compounds that act on the central nerous system and are of particular interest with regard to their anticonvulsant sedative action.

It has now been found that the compounds of general formula I with a free amino group in position 10 have a remarkable effect in increasing bladder capacity. This regulatory effect on the threshold of the urination reflex indicates that the compounds of which the therapeutic use constitutes the subject of the present invention represent a valid means of treating urinary incontinence.

The present invention therefore relates to the application and use of a 10-amino derivative corresponding to formula I and its derivatives to prepare a drug intended for the treatment—both prophylactic and curative—of urinary incontinence.

The invention also relates to a pharmaceutical preparation intended for the treatment of urinary incontinence, which preparation contains as active ingredient an effective quantity of a 10-amino compound of formula I, or of a pharmaceutically acceptable salt of said compound, combined with one or more pharmaceutical excipients or vehicles.

It is also possible to use as the active ingredient, rather than the free amino derivative of formula I, a derivative of the same in which the amino function in position 10 is protected, such as, for example, the acetyl derivative.

Compounds constituting the subject of the present invention are suitable for oral administration in the form of, for example: tablets, capsules, powders, granules, syrups; suppositories and others.

In the pharmaceutical formulations suitable for administration the compounds constituting the subject of the invention are present in a quantity between 0.1% and 30%, preferably between 0.5% and 10% by weight in a mixture with the usual excipients such as, for example: gelling agents, auxiliary substances for tablets, auxiliary substances for gelatine capsules or even auxiliary substances such as, for example, antioxidants, dispersing agents, emulsifiers, antifoam agents, flavor correctors, preservatives, solubilizing agents and colorants.

It is advisable for the active compound to be administered in one or more daily doses of between 0.1 and 100 mg/kg body weight, preferably between 0.5 and 30 mg/kg body weight.

The optimum dose and method of administration of the active compounds required in each individual case can easily be determined by each expert on the basis of his experience.

Pharmaceutical formulations comprising combinations of one or more compounds that constitute the subject of the invention, which compounds can be combined with one or more pharmaceutically active compounds belonging to other groups of drugs, constitute part of the present invention.

A number of examples are given below setting out methods for preparing the compounds that constitute the subject of the invention, the activity demonstrated and pharmaceutical formulations containing the active substances.

EXAMPLE 1

10-amino-5,6-dihydro-11H-dibenzo(be)azepine-6,11-dione

To 22 g 1-amino-anthraquinone, dissolved in 60 ml concentrated sulfuric acid, are added, a little at a time, keeping the temperature at 30°–40° C., 8 g sodium azide. When the addition is complete, the mixture is kept at ambient temperature, with stirring, for a further 12 hours, then poured into 1 liter of very cold water. A base is added to give a slightly acid pH, and the precipitate is filtered and washed thoroughly. The crude product obtained is crystallized alternately from dioxane and ethanol until a compound with a melting point of 274°–8° C. is obtained.

EXAMPLE 2

10-acetamido-5,6-dihydro-11H-dibenzo(b,e)azepine-6,11-dione

To 2.5 g 10-amino-5,6-dihydro-11H-dibenzo(b,e)azepine-6,11-dione in 50 ml dioxane are added 2 ml anhydrous acetic acid. This mixture is kept at reflux for 2 hours then brought almost to dryness under reduced pressure, and then poured into water, filtered and dried. Yield 2 g (ethanol): melting point 270°–2° C.

EXAMPLE 3

10-amino-5-methyl-5,6-dihydro-11H-dibenzo(b,e)azepine-6,11-dione

To 5 g 10-amino-5,6-dihydro-11H-dibenzo(b,e)azepine-6,11-dione in 25 ml dimethylformamide are added 0.8 g 60% sodium hydride in mineral oil and then 1.5 ml methyl iodide. After leaving for 24 hours at ambient temperature, with stirring, the mixture is poured into water, filtered and dried: melting point 171°-3° C. (water).

EXAMPLE 4

10-acetamido-5-methyl-5,6-dihydro-11H-dibenzo(b,e)azepine-6,11-dione

To 2 g 10-acetamido-5,6-dihydro-11H-dibenzo(b,e)azepine-6,11-dione suspended in 20 ml dimethylformamide are added 710 mg sodium methylate in 10 ml methanol. After keeping at ambient temperature for 30 minutes, 2.5 ml methyl iodide are added and the mixture then kept at ambient temperature for 24 hours. It is then poured into water, filtered, dried and crystallized from ethanol: yield 1.6 g, melting point 203°-204° C.

EXAMPLE 5

Preparation of 300 mg tablets 100 g 10-amino-5,6-dihydro-11H-dibenzo(b,e)azepine-6,11-dione, 100 g lactose, 5.6 g starch, 40 g microgranular cellulose are granulated with water q.s.; the wet mass is passed through a 15 mesh stainless steel sieve and dried in a cabinet with forced circulation of hot air; the granules obtained, after being passed again through a 25 mesh stainless steel sieve, are lubricated with 4 g magnesium stearate and undergo tableting to give 300 mg tablets.

EXAMPLE 6

Preparation of hard gelatine capsules 100 g 10-acetamido-5-methyl-5,6-dihydro-11H-dibenzo(b,e)azepine-6,11-dione, 50 g lactose, 30 g starch, 20 g crystalline cellulose, 1 g magnesium stearate are granulated with water q.s.: the wet mass is passed through a 15 mesh stainless steel sieve and dried in a cabinet with forced circulation of hot air: the granules obtained are passed again through a 25 mesh stainless steel sieve, then measured into capsules with a suitable filling machine.

EXAMPLE 7

Soft gelatine capsules 100 g 10-acetamido-5-methyl-5,6-dihydro-11H-dibenzo(b,e)azepine-6,11-dione are suspended in 93.1 g liquid glycerides of saturated fatty acids (C8-10), 53.4 g solid glycerides of saturated fatty acids (C8-18) and 6.5 g soybean lecithin; the suspension obtained is passed through a colloidal mill for the time necessary to obtain a homogeneous paste that is then filled into soft gelatine capsules with the aid of a suitable automatic machine.

The biological activity of the compounds constituting the subject of the present invention in treating bladder incontinence was evaluated in the test of hyperreflexia of the detrusor muscle induced by the administration of 6-hydroxydopamine (6-OHDA) as described by Maggi et al. (Drug Devl. Res. 10, 157, 1987). The urination reflex was evoked by the transvesical infusion of physiological saline. The quantity of saline needed to evoke the urination reflex is proportional, therefore, to the bladder capacity.

The administration to rats of two doses of 6-hydroxydopamine (OHDA) (25 mg/kg i.p. 24 hours before and then 50 mg/kg i.v. 18 hours before) reduces bladder capacity by approximately 75%, thus simulating a condition of hyperreflexia of the detrusor muscle. Administration in doses of 40 mg/kg by mouth of the compounds constituting the subject of the present invention reverses the hyperreflexia induced by 6-OHDA, restoring the bladder capacity to normal values.

We claim:

1. Method of treating urinary incontinence in a subject suffering therefrom, comprising administering to such a subject a urinary incontinence reversing effective amount of a 10-amino-5,6-dihydro-11H-dibenzo(b,e)azepine-6,11-dione compound of the formula

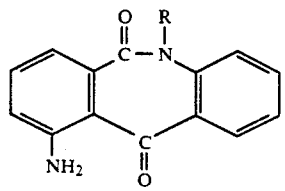

wherein R is hydrogen or lower alkyl, and optionally the amino function in the 10-position is blocked by an acetyl group, and the therapeutically acceptable salts thereof.

2. Method of claim 1 wherein R is lower alkyl having from 1 to 5 carbon atoms.

3. Method of claim 1 wherein R is methyl.

4. Method of claim 1 wherein the amino function in the 10-position is blocked by an acetyl group.

5. Method of claim 1 wherein R is lower alkyl having from 1 to 5 carbon atoms, and the amino function in the 10-position is blocked by an acetyl group.

6. Method of claim 1 wherein said compound is 10-amino-5,6-dihydro-11H-dibenzo(b,e)azepine-6,11-dione.

7. Method of claim 1 wherein said compound is 10-amino-5-methyl-5,6-dihydro-11H-dibenzo(b,e)azepine-6,11-dione.

8. Method of claim 1 wherein said compound is 10-acetamido-5,6-dihydro-11H-dibenzo(b,e)azepine-6,11-dione.

9. Method of claim 1 wherein said compound is 10-acetamido-5-methyl-5,6-dihydro-11H-dibenzo(b,e)azepine-6,11-dione.

10. Method of claim 1 wherein said compound is orally administered.

11. Method of claim 1 wherein said compound is administered in a dose of about 0.1-100 mg/kg body weight.

12. Method of treating urinary incontinence in a subject suffering therefrom, comprising administering to such a subject a composition of a urinary incontinence reversing effective amount of a 10-amino-5,6-dihydro-11H-dibenzo(b,e)azepine-6,11-dione compound of the formula

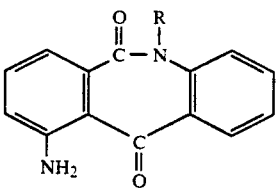

wherein R is hydrogen or lower alkyl, and optionally the amino function in the 10-position is blocked by a protective group, and the therapeutically acceptable salts thereof, in admixture with a pharmaceutically acceptable excipient or vehicle, in which said compound is present in an amount of about 0.1–30% by weight of the mixture.

13. Method of claim 12 wherein R is lower alkyl having from 1 to 5 carbon atoms.

14. Method of claim 12 wherein R is methyl.

15. Method of claim 12 wherein the amino function in the 10-position is blocked by an acetyl group.

16. Method of claim 12 wherein R is lower alkyl having from 1 to 5 carbon atoms, and the amino function in the 10-position is blocked by a acetyl group.

17. Method of claim 11 wherein said compound is 10-amino-5,6-dihydro-11H-dibenzo(b,e)azepine-6,11-dione.

18. Method of claim 12 wherein said compound is 10-amino-5-methyl-5,6-dihydro-11H-dibenzo(b,e)azepine-6,11-dione.

19. Method of claim 11 wherein said compound is 10-acetamido-5,6-dihydro-11H-dibenzo(b,e)azepine-6,11-dione.

20. Method of claim 12 wherein said compound is 10-acetamido-5-methyl-5,6-dihydro-11H-dibenzo(b,e)azepine-6,11-dione.

21. Method of claim 12 wherein said composition is orally administered.

22. Method of claim 12 wherein said compound is administered in a dose of about 0.1–100 mg/kg body weight.

* * * * *